US005527909A

United States Patent [19]
Brennan et al.

[11] Patent Number: 5,527,909
[45] Date of Patent: Jun. 18, 1996

[54] SINGLE SOURCE METALLOORGANIC PRECURSORS TO TYPE II-VI SEMICONDUCTORS

[75] Inventors: John Brennan, Highland Park; Yifeng Cheng, Edison, both of N.J.

[73] Assignee: Rutgers, The State University of New Jersey, New Brunswick, N.J.

[21] Appl. No.: 275,618

[22] Filed: Jul. 14, 1994

[51] Int. Cl.$^6$ ............................... C07F 3/06; C07F 3/08; C07D 207/00; C07D 209/00
[52] U.S. Cl. ............................ 544/64; 546/2; 546/153; 548/403; 556/130
[58] Field of Search ............................ 556/130; 546/2, 546/153; 544/64; 548/403

[56] References Cited

U.S. PATENT DOCUMENTS 5,157,136  10/1992  Arnold ................................ 556/9

OTHER PUBLICATIONS

Ruiz et al., Chem. Abs., vol. 100, No. 22, Abs. No. 180182a, (1984).
M. B. Hursthouse et al., (1991) Organometallics, vol. 10, pp. 730–732.
Y. Takahashi et al. (1980) Journal of Crystal Growth, vol. 50, p. 491.
J. O. Williams et al. (1992) Thin Solid Films vol. 87, L1.
D. M. Frigo et al., (1989) Journal of Crystal Growth, vol. 96, pp. 989.
G. N. Pain et al. (1989) Polyhedron, vol. 9, #7, pp. 921–929.
J. G. Brennan et al, (1990) Chemistry of Materials, vol. 2, pp. 403–409.
S. M. Stuczynski et al., (1989) Inorganic Chemistry, vol. 28, #25, pp. 4431–4432.
D. W. Kisker, (1989), Journal of Crystal Growth, vol. 98, pp. 127–139.
Phillip J. Bonasia et al, (1992), Journal of Inorganic Chemistry, vol. 31, pp. 2508–2514.
Saunders, A. et al., (1986), Ternary Multiary Compound Proc. Int. Conf. 7th, (see Chem. Abst. (1988) vol. 108, #662266.
Bochmann et al., (1991), Journal of Chemical Society, Dalton Transactions, pp. 2317–2329.

*Primary Examiner*—Porfirio Nazario-Gonzales
*Attorney, Agent, or Firm*—John F. Ritter

[57] ABSTRACT

The present invention relates a precursor metal organic compound of the formula:

$$2\text{-NR-Q-M-A}$$

wherein M is selected from the Group IIb elements of Zinc, Cadmium, of Mercury;

A is selected from R: Amide, alkyl having from 1 to 20 carbon atoms, aryl, substituted aryl, or -Q'-2-NR'L2 wherein L is selected from nothing or a Lewis base ligand, Q and Q' are each independently selected from Group VIa elements of sulfur, selenium, or tellurium; and 2-NR and 2-NR" are each independently selected from N-heterocyclic aryl or its derivatives.

In a preferred embodiment, A is -Q'-2-NR' and L is nothing, especially wherein 2-NR=2-NR', Q=Q'. Methods of producing these compounds are also disclosed. These precursor materials provide in a single compound the binary, tertiary, or quaternary metals in a ratio to each other that is controllable by a discerning choice of metal atoms and organic constituents. The metal alloys are useful in a variety of electronic applications, particularly in semiconductors.

22 Claims, No Drawings

SINGLE SOURCE METALLOORGANIC PRECURSORS TO TYPE II-VI SEMICONDUCTORS

The invention was made with Government support under the National Science Foundation, Grant No. CHE9204160, and as such the Government has certain rights to this invention.

BACKGROUND OF THE INVENTION

1. Field of the Invention

The present invention relates to the preparation of novel metal organic precursor compounds comprising at least one metal from Group IIb and at least one element from Group VIa of the Periodic Table. More specifically, these novel II/VI compounds are useful as single source metalloorganic tellurium, selenium, sulfur, zinc, cadmium or mercury containing precursors which are used in the preparation of semiconducting materials, e.g. as thin films, having precisely defined elemental ratios.

2. Description of the Related Art

Semiconducting thin-film alloys can be comprised of various combinations of elements from Group IIb(II) and VIa(VI) of the standard Periodic Table. These alloys are increasingly important due to their useful electronic, optoelectronic, magnetooptic and piezoelectric properties. These physical, chemical and electrical properties make the II/VI alloys of interest for a wide range of applications including, but not limited to, photovoltaic cells, infrared windows, light emitting diodes, and blue-green lasers.

In the conventional processing, the growth of II/VI thin films usually involves the use of two or more different volatile, toxic metal alkyl precursor compounds, i.e. one metalloorganic compound for each metallic element to be deposited. Each metalloorganic precursor has a different reactivity often causing undesirable pre-reactions to occur prior to mixing. Moreover, side reactions occur during processing which substantially limit the usefulness of the of metal alloy thin films which are produced.

These undesirable reactions can lead to difficulties in controlling the Group II/Group VI metal ratio in the resultant films, because one of the metal alkyl precursors is deposited before deposition of the desired metal alloy film on the substrate can occur. The toxicity of currently used II/VI precursor metalloorganic compounds also leads to considerable difficulties in storage, safety and environmental disposal. Moreover, the use of two or more metalloorganic compounds requires the extra capital expense of a second or third precursor compound line to the reactor in which the metal alloy is produced.

Considerable effort has been directed toward the synthesis of single source precursors to II–VI materials, with the majority of the work focused on the preparation of metal chalcogenolates $M(ER)_2$ (M=Zn,Cd,Hg; E=S,SE,Te R=organic). The thermal decomposition of Group IIb metal chalcogenolates to give binary ME materials has long been recognized. While these molecules would seem likely candidates for CVD processes, they are generally polymeric compounds. The suppression of polymer formation with the use of sterically demanding chalcogenolate ligands has been recently reported, and represents one possible way to enhance precursor volatility. However, these sterically saturated compounds show a tendency to reductively eliminate dichalcogenide to give elemental metal, rather than metal chalcogenide.

An alternative route to volatile precursors involves saturating the metal coordination sphere with strong neutral donor ligands. However, such ligands do not necessarily enhance compound volatility because the ligands tend to dissociate at temperatures lower than the temperatures at which the neutral complex sublimes. Moreover, this ligand dissociation process diminishes the utility of the precursor in metalloorganic chemical vapor deposition (MOCVD) processes.

Some general reports of the production of II/VI materials using separated metalloorganic compounds include, for example:

M. B. Hursthouse et al. (1991) *Oganometallics*, Vol. 10, pp 730–732, describes compounds of mixed alkyl tricarbonates of zinc and cadmium. These precursors are then used for deposition of semi conductors by metalloorganic chemical vapor deposition (MOCVD).

Y. Takaleaki et al. (1980) *Journal of Crystal Growth*, Vol. 50, p. 491, describes the preparation of precursors of cadmium or zinc dimethylthiophophinates for the production of cadmium sulfide or zinc sulfide.

J. O. Williams et al. (1992) *Thin Solid Films* Vol. 87, L1, describes the growth of highly ordered sulfide films using metal dimethylthiophosphinates.

A. Sounders et al. (1986) in "Ternary Multiary Compound" in *Proceedings in the International Conference 7th*, published in 1987, (see CA, 1988, Vol. 108, #66226H) describes the growth of sulfide films from zinc and cadmium thiocarbonates.

D. M. Frigo et al., (1989) *Journal of Crystal Growth*, Vol. 96, P. 989, describes sulfides of excellent crystallinity grown using bis(diethyldithiocarbonates).

M. Bochmann et al. (1989) *Angew. Chem. International Edition in English* Vol. 111, p. 414, discloses the preparation of low coordination number complexes of cadmium and zinc with sterically hindered thiols and selenols, such as 2,4,6-tri-tertiary-butylbenzene-thiol.

G. N. Pain et al. in *Polyhedron*, (1990) Vol. 9, #7, pp.921–929, discloses the preparation of organometallic cadmium, mercury and tellurium compounds which are used as precursors to metal alloys.

J. G. Brennan et al. in *Chemistry of Materials*, (1990) Vol. 2, pp.403–409, discloses the use of separate metalloorganic II/VI precursors useful in the preparation of metallic thin films.

S. M. Stuczynski et al. in *Inorganic Chemistry*, (1989), Vol. 28, #25, p.4431 and 4432, discloses the formation of metal-chalcogen bonds by the reaction of metal alkyl with silyl chalcogenides. However, they do not reach or suggest the preparation of all metals in a single precursor compound.

D. W. Kisher in *Journal of Crystal Growth*, (1989), Vol. 98, p.127–139, discusses the II/VI family of semiconductors alloys as obtained by organometallic vapor phase epitaxy (OMVPE), particularly in applied optoelectronics.

Phillip J. Bonasia et al. in *Inorganic Chemistry*, (1992), Vol. 31, pp.2508–2514, describes the preparation of homoleptic zinc, cadmium, and mercury tellurolates incorporating the bulky sitel anion. (sitel=TeSi(SiMe3)3).

Arnold (U.S. Pat. No. 5,157,136) disclose a single-source metalloorganic precursor used to produce II/VI materials. However, the present invention improves on all known precursors, including Arnold, by covalently binding a strong neutral donor atom to the chalcogenate functional group. This enhances compound volatility by decreasing polymer formation in the solid state, saturating the metal coordination sphere in the vapor phase and stabilizing gas phase species. Importantly, the present invention, unlike Arnold, eliminates the possibility of silicon incorporating impurities in the final solid state product. In the present invention, there is only one viable decomposition pathway because there is only one weak bond (C-E, E=S, Se, Te).

All of the references, patents, standards, etc. referenced in this application are incorporated herein by reference.

The problems in this art remain, i.e. the reactive precursors, undesirable pre-reactions, side reactions and non-volatility or low volatility. It would be extremely useful to have the metals of interest in a single, stable and volatile metalloorganic precursor compound so that the ratio of the metals deposited as an alloy upon decomposition can be more precisely controlled. The present invention provides such precursor compounds and processes to produce them.

SUMMARY OF THE INVENTION

It is an object of the present invention to provide a single-source metalloorganic precursor.

It is another object of the present invention to provide a metalloorganic precursor which is structurally simple so as to evolve stable organic materials which do not react further to contaminate the final product.

It is yet another object of the present invention to provide a metalloorganic precursor with sufficient volatility to be useful in the preparation of metallic thin films.

It is a further object of the present invention to provide a metalloorganic precursor capable of depositing the metals of interest in precise ratios.

It is another object of the present invention to provide a metalloorganic precursor with a lower toxicity.

The present invention relates to a metal organic compound of the formula:

wherein M is selected from the Group IIb elements of Zinc, Cadmium, and Mercury;

A and R are independently selected from amide, alkyl having from 1 t 20 carbon atoms, aryl, substituted aryl, or -Q'-2-NR'L2 wherein L is selected from nothing or a Lewis base ligand;

Q and Q' are each independently selected from Group VIa elements of sulfur, selenium, or tellurium; and 2-NR and 2-NR' are each independently selected from N-heterocyclic aryl or its derivatives.

Preferably, the metal compound has A as -Q'-2-NR and L is nothing, especially wherein 2-NR=2-NR', Q=Q'.

In one embodiment, Q is selenium, primarily wherein M is mercury.

In a preferred embodiment, the metal compound has 2-NR and 2-NR' as pyridinyl, more preferably, wherein Q and Q' are selenium.

In another embodiment, the metal compound has L as the Lewis base ligand which is independently selected from pyridine, substituted pyridine, pyrrole, substituted pyrrole, quinoline, morpholine, 2,2'-bipyridyl organic phosphine, organic arsine, alkyl ether, aryl ether, thioether, amine, chelate of diamines, diphosphines, diarsines, diethers or mixtures thereof.

In another embodiment, the present invention also concerns a process for the production of a metal organic compound of the formula:

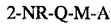

wherein M is selected from the Group IIb elements of Zinc, Cadmium, of Mercury;

A and R are independently selected from: amide, alkyl having from 1 to 20 carbon atoms, aryl, substituted aryl, or -Q'-2-NR'-L2 wherein L is selected from nothing or a Lewis base ligand, Q and Q' are each independently selected from Group VIa elements of sulfur, selenium, or tellurium; and 2-NR and 2-NR' are each independently selected from N-heterocyclic aryl or its derivatives.

which process comprises:

(A) contacting L'2-Z-2-NR wherein L' is independently selected from ligand L,

Z is independently selected from lithium, sodium, potassium, calcium, barium, or strontium; and 2-NR is defined hereinabove, with a metal powder Q wherein Q is defined hereinabove, in a polar solvent under an inert anhydrous atmosphere for between about 0.01 and 2 hr between −20° and +30° C.;

(B) contacting the product of step(A) with a strong or a weak acid to produce and separated by removal of the polar solvent to give

wherein Q, 2-NR are defined hereinabove;

(C) contacting the product of step(B) with:

(1) $MX_2$ salt wherein X is selected from a halogen, a nitrate, an organic acid, and the like in a 2:1 ratio in a polar solvent at between −20° C. and +30° C., and for between about 0.01 and 2 hr, or (2) $MR_2$ wherein R is selected from amide, alkyl having from 1 t 20 carbon atoms, aryl, substituted aryl, or -Q'-2-NR'L2 wherein L is selected from nothing or a Lewis base ligand in a 2:1 ratio in a polar solvent at between about −20° and +30° C., and for between about 0.01 and 2 hr, or (3) $M(R')_2$ or $MX_2$ wherein R' is independently selected from amide or R as defined hereinabove in a 1:1 ration in a polar solvent at between about −20° and +30° C. and for between about 0.01 and 2 hr, followed by treatment; with one H-Q-2-NR, where Q and 2-NR are defined above, in a polar solvent at between −20° C. and +30° C., and for between about 0.01 and 2 hr;

(D) recovering the metalloorganic compound of structure (I), where L is nothing; and (E) optionally contacting the product of step (D) with ligand L to produce the organometallic compound where L is a Lewis base.

In another aspect, the present invention relates to a process for the production of a binary, ternary or a quaternary metal alloy, which process comprises:

(a) subjecting the metalloorganic compound (I) described above to a temperature of between about 150° C. and 500° C., in an anhydrous vacuum between about ambient pressure to $10^{-6}$) Torr. (e.g. $10^{-2}$ to $10^{-6}$ Torr.), especially the metal alloy producing process wherein A is -Q'-2-NR' and Q=Q' and 2-NR=2-NR'.

DETAILED DESCRIPTION OF THE PREFERRED EMBODIMENTS

Definitions

As used herein:

"Alkyl" refers to all alkyl groups usually having 1 to 20 carbon atoms. All methyl to octyl straight chain branched, and 4,5 or 6 member hydrocarbon rings are also included.

"Aryl" refers to phenyl, naphthylene, anthracene, phenanthrene and the like. Aryl also includes groups such as —C-(phenyl)3, —C(4-methylphenyl)3, —C(4-methoxyphenol)3, and the like. Aryl also includes heterocyclic aryl groups such as pyridine, pyrrole, quinoline, furan, and the like. Hydrocarbon such as phenyl is preferred.

"X" refers to halogens, nitrate, organic acid and the like.

"Substituted aryl" refers to alkyl ($C_1$–$C_{20}$) or halogen substituted for one or more protons on the aryl ring. Generally 1,2 or 3 proton substitutions are preferred. Substituted aryl also includes substituted heterocyclic aryl groups.

"N-heterocyclic aryl" refers to pyridine, pyrrole, quinoline and the like.

"Substituted N-heterocyclic aryl" refers to alkyl ($C_1$–$C_{20}$) or halogen or amine or amide or nitro and the like substituted for one or more protons on the aryl ring. Generally 1,2 or 3 proton substitutions are preferred.

General Synthesis

A typical experiment is described to produce a symmetric (with reference to the M atom) metalloorganic compound. First, 2-NR-X and ZHQ or Z2Q in a N:1(n=0.1–10) molar ratio are combined, stirred, heated in anhydrous aprotic polar solvent, such as dimethylformamide (DMF), dimethylsulfoxide (DMSO), hexamethylphosphoramide (HMPA) or the like, or anhydrous protic polar solvent, such as alcohols or the like under a stream of nitrogen between about 20° C. to 35° C. for between about 5 minutes and one week. The corresponding 2-NR-Q-H or 2-NR-Q-Q-2-NR or L2Z-Q-2-NR is produced in good yield. When 2-NR-Q-Q-2-NR is treated with reducing reagent in anhydrous polar solvent, the corresponding L2Z-Q-2-NR is also obtained in almost quantitative yield with the addition of ligand L reagents.

Z is independently selected from alkali metals. Sodium is preferred.

Q is independently selected from sulfur, selenium, or tellurium. Selenium is preferred.

L is the Lewis base ligand which is independently selected from pyridine, substituted pyridine, pyrrole, substituted pyrrole, quinoline, morpholime, 2,2' bipyridyl organic phosphine, diarsines, diethers or mixtures thereof.

The compound M(-Q-2-NR)2 can be prepared by several routes, as follows:

(1) 2-NR-Q-H is contacted with $MX_2$ in a 2:1 equivalent ratio in polar solvent with or without some Lewis base at between −20° and +30° C. for between about 0.01 and 12 hrs.

Alternative (2), Z-Q-2-NR is contacted with $MX_2$ in a 2:1 equivalent ratio in polar solvent or water at between −20° and +30° C. for between about 0.01 and 12 hrs.

Alternative (3), 2-NR-Q-Q-2-NR is contacted with metal M in a 1:1 equivalent ratio in anhydrous polar solvent under N2 at between about 0.1 hour and one week.

Alternative (4), 2-NR-Q-H is contacted with $M(R)_2$ in 2:1 in a polar solvent at between about −20° C. and 30° C. (preferably ambient temperature) for between about 0.01 and 3 hr.

Alternative (5), 2-NR-Q-M-R" (leq) is contacted with 2-NR'-Q'-H in a polar solvent at between about −20° C. and 30° C. (preferably ambient temperature) for between about 0.01 and 3 hr.

Alternative (6), 2-NR-Q-M-X (leq) is contacted with Z-Q'-2-NR' in a polar solvent or water at between about −20° C. and 30° C. (preferably ambient temperature) for between about 0.01 and 3 hr.

Alternative (7), 2-NR-Q-M-X (leq) is contacted with H-Q'-2-NR' in a polar solvent or water with or without some Lewis base at between about −20° C. and 30° C. (preferably ambient temperature) for between about 0.01 and 3 hr.

To obtain a binary alloy, M and Q are as defined hereinabove for alternative 1,2 or 3, To obtain a ternary alloy, M and Q are as defined hereinabove and Q' is present and is different from Q in alternative (5,6) above.

To obtain ternary or quaternary (or higher) alloys, it is possible to physically combine the compounds produced in alternatives 1,2,3,4,5,6 or 7 above in a hot polar solvent and recover the mixed solid compounds upon cooling.

The metalloorganic compounds of the present invention are quasi-1D polymeric with weakly connected units. For this reason, they have the needed volatility to be able to be transferred within reaction lines and vessels under conventional inert atmospheric conditions. These properties are in stark contrast with those metalloorganic compounds of the art, which have a higher degree of polymerization or larger molecular weight and organometallic compounds which are essentially non-volatile.

Experimental Method used for Growth of II/VI Films

Any of the precursor materials are deposited on to substrates such as quartz or GaAs in the following manner. A quartz tube containing the precursor compound and a slice or wafer of the substrate material is placed inside a resistively heated tube furnace having a temperature gradient ranging from 100° C. to 600° C. along the length of the apparatus. The compound is placed at the cooler end of the tube while a stream of nitrogen or argon gas is passed through over the compound and toward the substrate. On impinging the hot substrate, the precursor compound decomposes, depositing a thin film of II/VI alloy. The volatile decomposition products are removed in the gas stream.

Alternatively, the above process can be carried out under high vacuum ($10^{-6}$ to $10^{-6}$ Torr) using the vapor pressure of the gaseous compound to transport the material to the substrate. In this case, the decomposition products condense in a part of the tube held at a much lower temperature (20°–40° C.).

Pyrolysis of Metalloorganic Compounds

The pyrolysis of the compounds by conventional means in the art is contemplated. For example, pyrolysis of Hg(SePy)2 proceeds as in the following equation:

Hg(SePy)2→HgSe+Py—Se—Py

Thus, exactly 50% of the selenium in the starting materials is converted to metal selenide. The remaining 50% of the selenium is removed from the system as stable, volatile Py—Se—Py.

General

The chemical agents, reagents and solvents described above are usually used as obtained from U.S. chemical supply plants, E.G. Aldrich Chemical Co. All syntheses were carried out under ultrapure nitrogen (JWS), using conventional drybox or Schlenk techniques. Melting points were taken in sealed capillaries, and are uncorrected. Power diffraction spectra were obtained from SCINTAG PAD V diffraction meter and monochromatized CuKα radiation. GCMS data were collected from 5890 Series II GAS CHROMATOGRAPH and HP 5971 mass selective detector. IR spectra were taken by diffuse reflectance in KBr using Perkin Elmer 1720X FTIR at 4 $cm^{-1}$ resolution from 4000–450 $cm^{-1}$. NMR spectra were recorded on a Varian XL 200 MHz NMR 24.5° C. Elemental analysis were preformed by Quantitative Technologies, Inc. (Salem N.J.).

EXAMPLE A

Selenol Intermediates

Sodium borohydride (2.1 g, 55.5 mmol) was added to a solution of selenium (4.0 g, 50.7 mmol) in a mixture of anhydrous ethanol and anhydrous chloroform (75 ml:25 ml) at 0° C. under $N_2$. After 30 minutes, the solution was brought to room temperature, and after an additional 30 minutes, the colorless solution was taken to dryness under vacuum to give a white powder (NaHSe). Ammonium chloride (0.5 g, 9.3 mmol), 2-bromopyridine (4.83 ml, 8.0 g, 50.7 mmol) and anhydrous dimethylformide (100 ml) were added and the mixture was heated to 85° C. in the dark for 15 hours. The solvent was removed from under the vacuum, and the yellow powder was washed first with cool water (100 ml) and then with a cool mixture of hexane and methanol (150 ml:50 ml). The solid was dissolved in $CH_2Cl_2$ (75 ml), the solution was filtered and cooled (−20° C.) to give yellow crystals of 2-Selenopyridine (4.5 g, 56.2%) that was identified by m.p(132° C.) and $^1H$ NMR ($CDCl_3$): 8.41(1H, broad), 7.86(1H,d), 7.71(1H,d), 7.38(1H,t) and 6.98(1H,t).

EXAMPLE B

Diselenide Intermediates (1) To a solution of 2-selenopyridine (2 g) in water (100 ml) air was bubbled for 12 hrs. 2,2'-dipyridyl diselenide separated and was collected by filtration. It was washed with a small amount of water and dried. The product was recrystallized from petroleum ether to give yellow needles; 1.5 g(78%), mp. 47.9° C.

(2) The product mixture in DMF from the preparation of 2-selenopyridine was cooled and then poured into 300 ml water and bubbled by air bubbles 12 hours. The solution was extracted by $Ch_2Cl_2$ (100 ml, 50 ml, 50 ml, 25 ml). The solvent was removed by vacuum. The residual yellow powder was recrystallized from petroleum ether to give yellow needle-like crystals.

EXAMPLE 1

Mercury-Selenium Precursor

2-Selenopyridine (2.0 g, 12.7 mmol) was dissolved in $CH_2Cl_2$ (100 ml), and $Hg(Ac)_2$ (2.07 g, 6.37 mmol) was added to the solution under vigorous stirring in the dark. After 10 minutes, the solution was colorless. The solution was filtered, concentrated to Ca. 50 ml, and cooled (0° C.) to give colorless needle-like crystals; a second, third, and fourth crop were isolated in identical fashion and combined to give $Hg(SeNC_5H_4)_2$ (3.07 g, 92%; m.p. 141.7° C. (dec. 183° C.)). The compound sublimes without decomposition (110° C., 0.10 mmHg).

IR: 1570(s), 1551(s), 1444(s), 1409(s), 1275(m), 1149(m), 1109(s), 1080(s), 1042(m), 983(m), 985(w), 879(w), 744(s), 694(s), 618(w), 467(m) $cm^{-1}$.

$^1H$ NMR ($CDCl_3$, 200 mHz, 20° C.): 8.12(d, 1H), 7.40(m, 2H), 7.01 (d, 1H)

Anal. calcd. for $HgC_{10}H_8N_2Se_2$; C23.3; H, 1.57; N, 5.44% Found: C 23.3; H,1.55; N, 5.35

EXAMPLE 2

Cadmium-Selemium Precursor

2-Selenopyridine (2.5 g, 15.9 mmol) was dissolved in methanol (100 ml) with vigorous stirring. Cadmium 2-ethylhaxanoate (3.15 g, 7.96 mmol) was added to the yellow solution to give a white precipitate. The precipitate was collected by filtration and washed by methanol (100 ml), to give a white solid (3.25 g, 90%). X-ray quality crystals were isolated by dissolving a portion of the white solid (1.00 g) in pyridine at 100° C.; an air bubbler was connected to the apparatus over 4 days; then colorless crystals (0.20 g) were collected along the edge of the evaporating pyridine solution (m.p. 210°–215° C.(dec)). The compound sublimes without decomposing (185° C., 0.1 mmHg).

IR: 1578(s), 1547(s), 1470(w), 1443(s), 1414(s), 1265(m), 1231(w), 1151(m) 1115(s), 1079(m), 1041(m), 1003(m), 765(m), 750(s), 698(m), 637(m) and 473(m) $cm^{-1}$.

$^1H$ NMR (DMSO): 7.80(1H,d), 7.47(1H,t) and 6.93(1H, t).

Anal. Calcd. for $CdC_{10}H_8N_2Se_2$: C, 28.2; H, 1.89; N, 6.57. Found C, 28.6; H, 2.20; N, 6.31.

While only a few embodiments of the invention have been shown and described herein, it will become apparent to those skilled in the art that various modifications and changes can be made in the process to produce a single stable precursor compound having two or more metal atoms useful to produce metal alloys having a defined metal atom ratio and the precursor thereof without departing from the spirit and scope of the present invention. All such modifications and changes coming within the scope of the appended claims are intended to be carried out thereby.

We claim:

1. A single source II–VI semiconductor precursor of the formula:

2-NR-Q-M-A

Wherein M is selected from the Group IIb elements of zinc, cadmium, or mercury;

A is selected from amide, alkyl having from 1 to 20 carbon atoms, aryl, substituted aryl, or -Q'-2-NR'L2 wherein L is selected from nothing or a Lewis base ligand;

Q and Q' are each independently selected from Group VIa elements of sulfur, selenium, or tellurium;

2-NR and 2-NR' are each independently selected from N-heterocyclic aryl or its derivatives; and which sublimes and subsequently decomposes between about 110° C. and 500° C.

2. The metal compound of claim 1 wherein A is -Q-2-NR' and L is nothing.

3. The metal compound of claim 2 wherein 2-NR=2-NR', Q=Q'.

4. The metal compound of claim 3 wherein 2-NR= pyridinyl.

5. The metal compound of claim 4 wherein Q is selenium.

6. The metal compound of claim 4 wherein Q is selected from sulfur and tellurium.

7. The metal compound of claim 5 wherein M is cadmium.

8. The metal compound of claim 5 wherein M is mercury.

9. The metal compound of claim 5 wherein M is zinc.

10. The metal compound of claim 5 wherein 2-NR= substituted 2-pyridinyl.

11. The metal organic compound of claim 1 wherein L, the Lewis base ligand, is present and is independently selected from pyridine, substituted pyridine, pyrrole, substituted pyrrole, quinoline, morpholime, 2,2'bipyridyl organic phosphine, organic arsine, alkyl ether, aryl ether, thioether, amine, chelate of diamines, diphosphines, diarsines, diethers or mixtures thereof.

12. The metal organic compound of claim 8 wherein the L is tetrahydrofuran (THF), or tetramethylenediammine (TMEDA) or dimethoxyethane (DME).

13. The metal organic compound of claim 9 wherein the L is THF, or TMEDA or DME.

14. The metal organic compound of claim 10 wherein the L is THF, or TMEDA or DME.

15. The metal organic compound of claim 5 wherein L, the Lewis ligand, is present and is independently selected from pyridine, substituted pyridine, pyrrole, substituted pyrrole, quinoline, morpholime, 2,2'bipyridyl organic phosphine, organic arsine, alkyl ether, aryl ether, thioether, amine, chelate of diamines, diphosphines, diarsines, diethers or mixtures thereof.

16. The metal compound of claim 15 where in M is cadmium.

17. The metal compound of claim 15 where in M is mercury.

18. The metal compound of claim 15 where in M is zinc.

19. A process for the production of a metal organic compound of the formula:

2-NR-Q-M-A

Wherein M is selected from the Group IIb elements of zinc, cadmium, or mercury;

A is selected from amide, alkyl having from 1 to 20 carbon atoms, aryl, substituted aryl, or -Q'-2-NR'L2 wherein L is nothing or a Lewis base ligand, Q and Q' are each independently selected from Group VI elements of sulfur, selenium, or tellurium, and 2-NR and 2-NR' are each independently selected from N-heterocyclic aryl or its derivatives, which process comprises:

(A) contacting L'2-Z-2-NR wherein L' is independently selected from ligand L,

Z is independently selected from lithium, sodium, calcium, barium, or strontium; and 2-NR is defined hereinabove, with a metal powder Q wherein Q is defined hereinabove, in a hydrocarbon solvent under an inert anhydrous atmosphere for between about 0.01 and 2 hours at between about −20° and +30° C.;

(B) contacting the product of step (A) with a strong or weak acid to produce and separate by removal of the hydrocarbon solvent

H-Q-2-NR where Q, 2-NR are defined hereinabove;

(C) contacting the product of step(B) with:

(1) $MX_2$ salt, wherein X is independently selected from a halogen, a nitrate, or an organic acid, in a 2:1 ratio in a polar solvent at between −20° and +30° C., and for between about 0.01 and 2 hour, or (2) $MR_2$, wherein R is independently selected from an amide, alkyl having between 1 and 20 carbon atoms, aryl, substituted aryl or -Q'-2-NR'-L2 wherein L is selected from nothing or a Lewis base ligand, in a 2:1 ratio in a polar solvent at between about −20° to +30° C., and for between about 0.01 and 2 hour, or (3) $M(R')_2$ or $MX_2$ wherein R' is independently selected from amide or R as defined hereinabove in a 1:1 ration in a hydrocarbon solvent at between about −20° to +30° C., and for between about 0.01 and 2 hour, followed by treatment; with one equient of H-Q-2-NR, where Q and 2-NR are defined above, in a polar solvent at between about −20° to +30° C., and for between about 0.01 and 2 hour;

(D) recovering the metalloorganic compound of structure (I), where L is nothing; and (E) optionally contacting the product of step(D) with ligand L to produce the organometallic compound where L is a Lewis base.

20. The process of claim 19 wherein L is present and is a Lewis base.

21. A process for the production of a di-, tri-, or tetrametal alloy, which process comprises:

(F) subjecting the metalloorganic compound step(D) or step(E) of claim 19 to a temperature of between about 150° and 500° C. in an anhydrous vacuum between about ambient pressure to $10^{-6}$ Torr.

22. The process of claim 19 wherein A is -Q-2-NR' and 2-NR=2-NR' Q=Q', and L is nothing.

* * * * *